United States Patent

Goethel et al.

[11] 4,109,656
[45] Aug. 29, 1978

[54] APPARATUS FOR USE WITH INSUFFLATORS

[75] Inventors: James Herbert Goethel, West Chester; Edwin Lowe Sohngen, Cincinnati, both of Ohio

[73] Assignee: Sybron Corporation, Rochester, N.Y.

[21] Appl. No.: 766,256

[22] Filed: Feb. 7, 1977

[51] Int. Cl.² ............................................. A61M 13/00
[52] U.S. Cl. .................................... 128/266; 128/208
[58] Field of Search ............... 128/266, 265, 208, 184, 128/213 R, 2 A, 145.8, 185

[56] References Cited

U.S. PATENT DOCUMENTS

| 3,771,552 | 11/1973 | Watanabe | 128/2 A X |
| 3,777,742 | 12/1973 | Aumiller et al. | 128/2 A |
| 3,881,463 | 5/1975 | LeMon | 128/2 A |

*Primary Examiner*—Robert W. Michell
*Assistant Examiner*—Henry J. Recla
*Attorney, Agent, or Firm*—Theodore B. Roessel; J. Stephen Yeo

[57] ABSTRACT

Apparatus for use with an insufflator. During the first part of an inhalator cycle, a patient is connected to ambient air but during the latter part of the inhalator cycle the patient is connected to the insufflator. This enhances the desired exposure of the patient's upper airways to the product of the insufflator.

1 Claim, 1 Drawing Figure

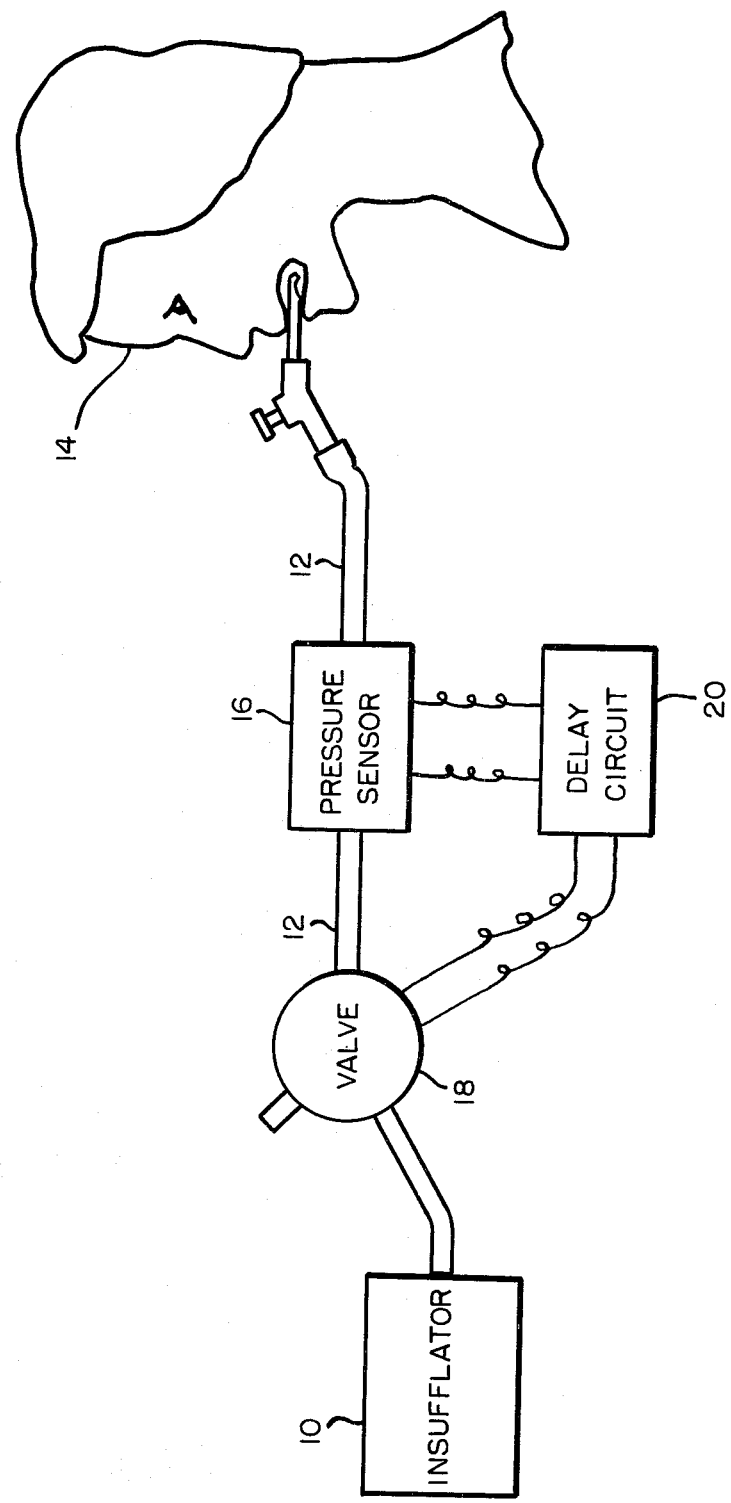

APPARATUS FOR USE WITH INSUFFLATORS

BACKGROUND OF THE INVENTION

This invention relates to apparatus for insufflating the airways of a human with a radiopaque powder such as powdered tantalum for the purpose of preparing the airway for radiologic study, and more particularly is directed towards apparatus for use with insufflators.

The use of powdered tantalum as a medium for bronchography is explained in "Investigative Radiology", Vol. 3, No. 4, July-August 1968 (pp. 229-238) and in "Radiology", Vol. 94, No. 3, March 1970 (pp. 547-553), these publications also disclosing apparatus for insufflating the airways. The latter publication suggests that insufflation of tantalum may be effected either by a catheter method or by an inhalation method, and in each instance, a cloud of tantalum dust is generated by blowing air into a pile of powdered tantalum stored in a chamber defined within a container. With the catheter method, the tantalum dust in the cloud is blown from the chamber and into the airways of the patient via a catheter tube while, with the inhalation method, the dust is sucked into the airways as the patient inhales on a tube leading from the chamber. The inhalation method is preferred in most cases in order to avoid the need for a catheter but it is sometimes necessary to use a catheter if it is desired to outline a particular area of the bronchus or with infants or patients who may not be completely healthy. We are presently concerned with the inhalation method.

Another example of apparatus for producing tantalum insufflation is disclosed in U.S. Pat. No. 3,777,742. Tantalum Insufflator issued Dec. 11, 1973 to Aumiller et al.

By sucking upon a breathing tube connected to a tantalum insufflator the patient inhales tantalum laden air. It is known that air breathed in the latter part of the inhalator cycle goes to the upper lung airways. This is also the last part of the airway to receive tantalum and thus the most difficult to accomplish.

It is, therefore, the object of this invention to provide simple means to enhance the coating of the upper lung airways.

SUMMARY OF THE INVENTION

A patient during a inhalation cycle is connected first to ambient air and then, during the latter part of the cycle, to a insufflator. This is accomplished by a pressure sensor which transmits a signal when inhalation is commenced upon a breathing tube. After a preselected delay a diverter valve switches the air input of the patient from ambient to the insufflator output.

BRIEF DESCRIPTION OF THE DRAWING

FIG. 1 illustrates the preferred embodiment of the invention.

DETAILED DESCRIPTION OF THE PREFERRED EMBODIMENT

We have found that the coating of the airways of the upper lungs can be enhanced without overloading the lower linings by allowing tantalum to be introduced into the inhaled air at some selectable point in the inhalation cycle. Apparatus suitable for practicing our invention is found in FIG. 1.

A tantalum insufflator 10, such a disclosed in U.S. Pat. No. 3,777,742, is provided with a breathing tube 12 upon which a patient 14 may suck.

A sensitive pressure sensor 16, of known design, is in communication with the breathing tube 12.

Interposed between the sensor 16 and the insufflator 10 is an electrically controlled diverter valve 18 which is arranged so that ambient non-laden air is normally connected to the breathing tube 12.

Sensor 16 transmits a signal upon the onset of inhalation. A known signal delay circuit 20 or timer may delay the signal to a preselected time. Upon the expiration of the preselected time period after the onset of inhalation a signal is sent from delay circuit 20 to the diverter valve 18. The diverter valve upon receipt of this second signal switches the patient's air path from direct ambient to the insufflator.

Various features, not shown, such as lights indicating inhalation, readouts showing elapsed time of inhalation and variable delay times may be incorporated in this apparatus.

We claim:

1. Apparatus for use with an insufflator comprised of:
an insufflator having an output;
a breather tube switchably connected to the output of said insufflator and to ambient air;
pressure sensor means arranged in communication with said breather tube so as to transmit a first signal when a patient inhales upon said tube;
delay circuit means being in electrical communication with said sensor and transmitting a second signal a predetermined time after said first signal but during the latter part of said inhalation cycle; and
a diverter valve connected between said breather tube and the output said insufflator and including means in electrical communication with said delay circuit and responsive to said second signal to first connect the patient to ambient air and then, upon receipt of the second signal, to switch the patient to the output of said insufflator.

* * * * *